United States Patent
Yassinzadeh et al.

[11] Patent Number: 6,103,196
[45] Date of Patent: Aug. 15, 2000

[54] FLOW DETECTION APPARATUS AND METHOD

[76] Inventors: Zia Yassinzadeh, 11240 Mount Hamilton Rd., San Jose, Calif. 95140; Paul J. Lingane, 2613 Read Ave., Belmont, Calif. 94002

[21] Appl. No.: 09/053,195

[22] Filed: Apr. 1, 1998

Related U.S. Application Data

[63] Continuation of application No. 08/579,367, Dec. 27, 1995, Pat. No. 5,736,404.

[51] Int. Cl.⁷ ............................ G01N 33/86; G01N 21/03
[52] U.S. Cl. ............................ 422/73; 422/63; 422/81; 422/82.05; 422/102; 436/52; 436/63; 436/69; 436/174; 436/179; 436/165
[58] Field of Search .................. 422/99–102, 63, 422/81, 82.05, 73; 436/148, 150, 177, 165, 169, 180, 52, 63, 69, 174, 179; 73/863.11, 863.12, 864.52, 864.61; 128/763, 764, 765

[56] References Cited

U.S. PATENT DOCUMENTS

| | | |
|---|---|---|
| 3,486,859 | 12/1969 | Greiner et al. . |
| 3,518,057 | 6/1970 | Giordano . |
| 3,640,267 | 2/1972 | Hurtig et al. . |
| 3,799,742 | 3/1974 | Coleman . |
| 3,821,643 | 6/1974 | Bostick et al. . |
| 3,890,098 | 6/1975 | Moreno . |
| 3,905,769 | 9/1975 | Carroll et al. . |
| 4,088,448 | 5/1978 | Lilja et al. . |
| 4,195,524 | 4/1980 | Hansen . |
| 4,627,445 | 12/1986 | Garcia et al. . |
| 4,637,403 | 1/1987 | Garcia et al. . |
| 4,659,550 | 4/1987 | Schildknecht . |
| 4,753,776 | 6/1988 | Hillman et al. . |
| 4,756,884 | 7/1988 | Hillman et al. . |
| 4,780,418 | 10/1988 | Kratzer . |
| 4,797,369 | 1/1989 | Mintz . |
| 4,952,373 | 8/1990 | Sugarman et al. . |
| 5,072,610 | 12/1991 | Martinoli et al. . |
| 5,147,607 | 9/1992 | Mochida . |
| 5,232,667 | 8/1993 | Hieb et al. . |
| 5,298,224 | 3/1994 | Plum . |
| 5,302,348 | 4/1994 | Cusack et al. . |
| 5,372,946 | 12/1994 | Cusak et al. . |

*Primary Examiner*—Long V. Le
*Attorney, Agent, or Firm*—Townsend and Townsend and Crew LLP

[57] ABSTRACT

Fluid sample tester assembly (12) comprises a cartridge (6) having a pressure chamber (22) and entrance port (20) connected by a passageway (24). An analyte reagent (36) is positioned along the fluid passageway so that when a liquid sample (28) is drawn through the entrance port into the passageway, the analyte reagent mixes with the sample. The sample is preferably drawn into the cartridge by temporarily reducing the volume of the pressure chamber, applying the sample to the entrance port and then returning the pressure chamber to its initial volume; this can also be done by heating the chamber, contacting the sample and then cooling the chamber. The end of the sample defines a boundary surface (30) along the fluid passageway. Positive and negative pressure is applied to the sample to cause the boundary surface to oscillate within the passageway. The position of the boundary surface is continuously monitored so that continuous boundary position data is obtained and is analyzed to obtain a flow-related characteristic, typically speed of coagulation, of the sample.

10 Claims, 8 Drawing Sheets

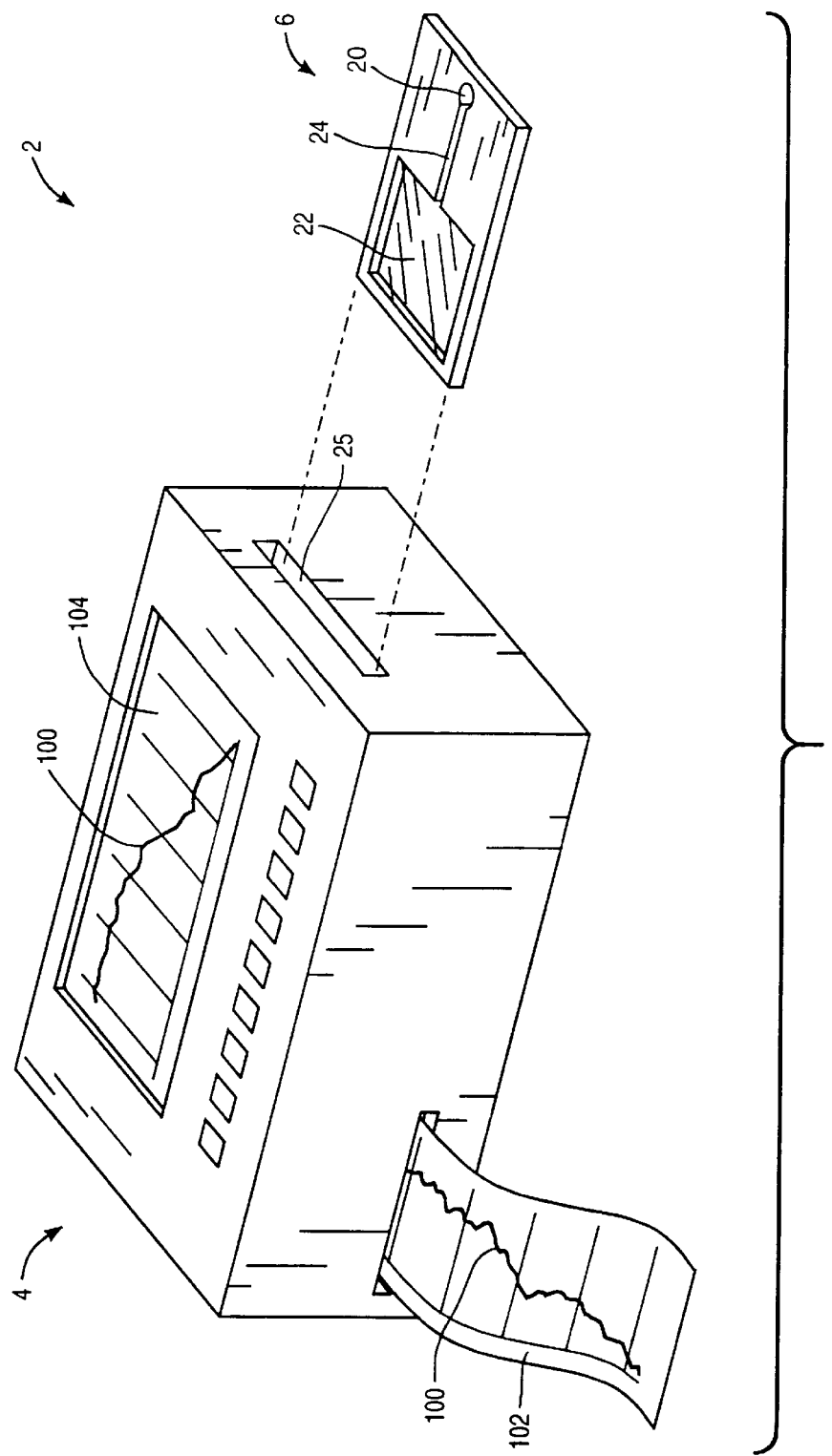
FIG_1

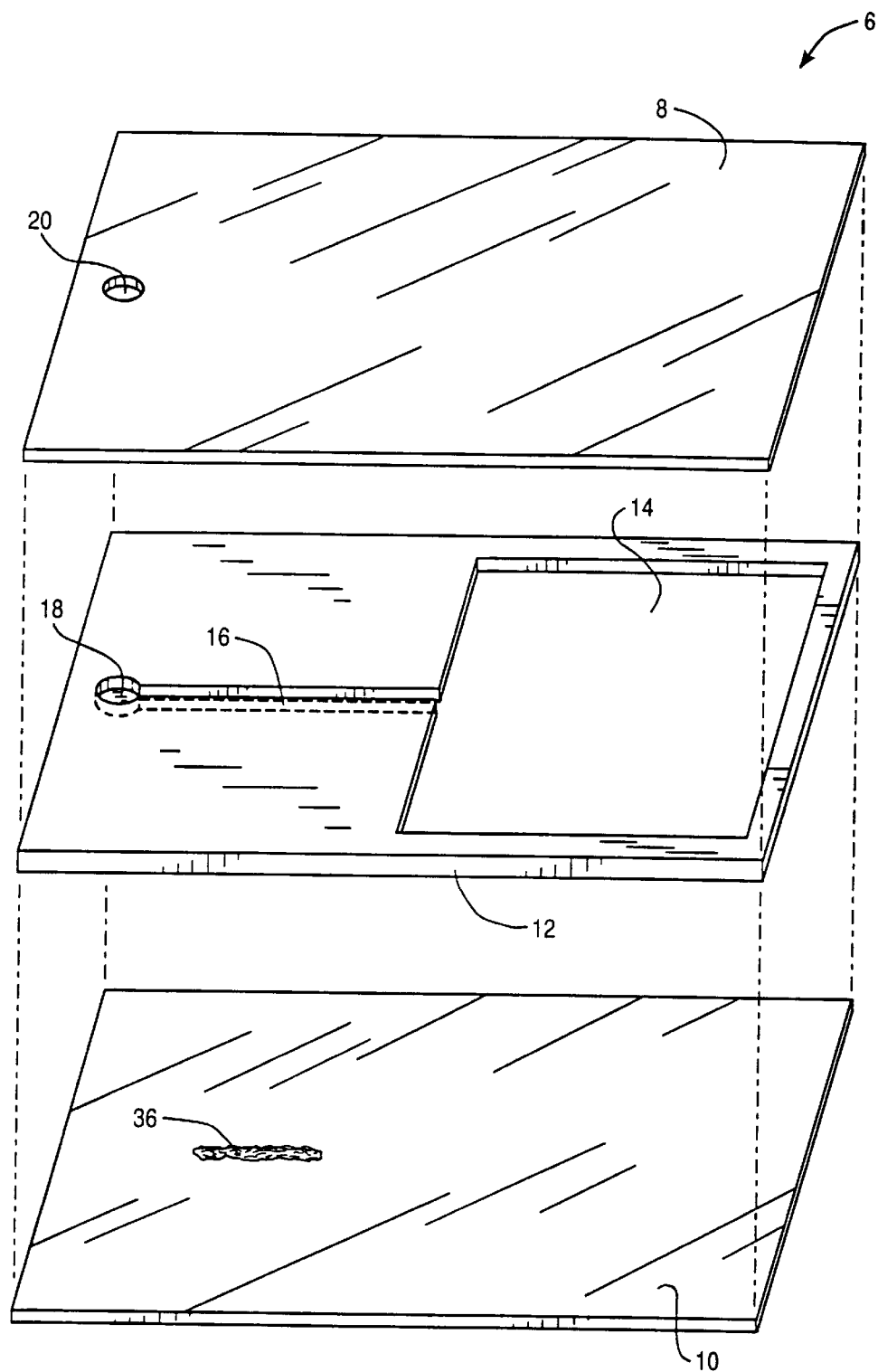
FIG_2

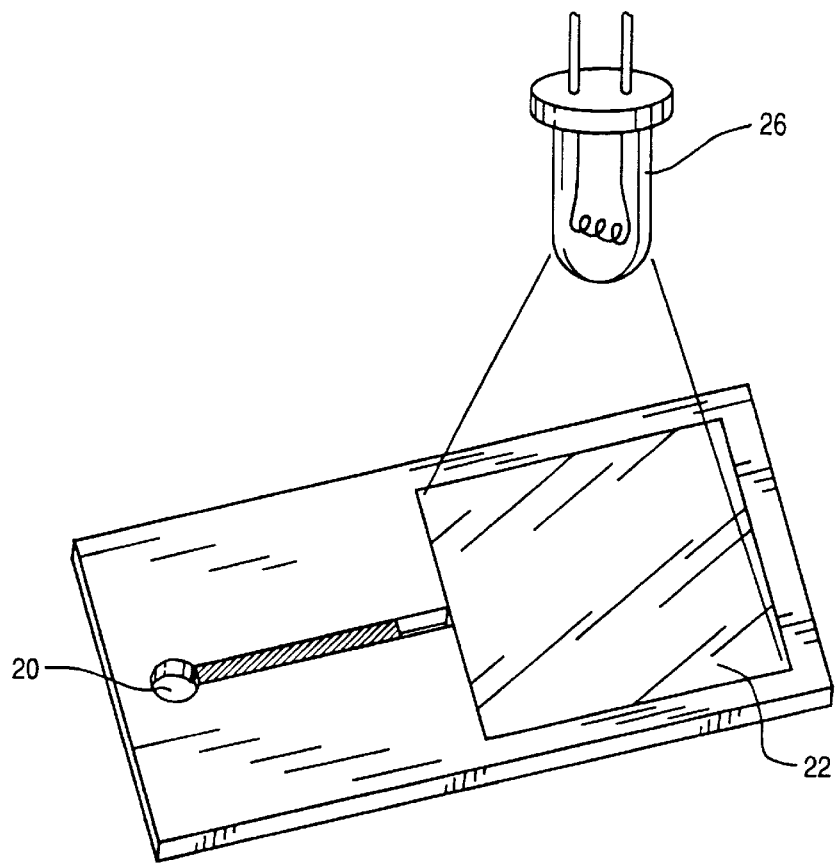
FIG_3
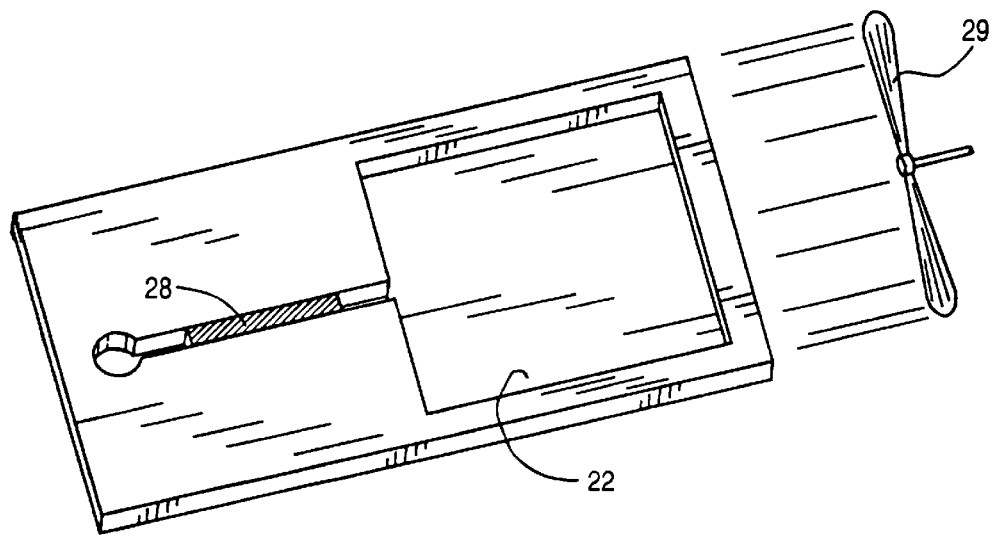
FIG_4

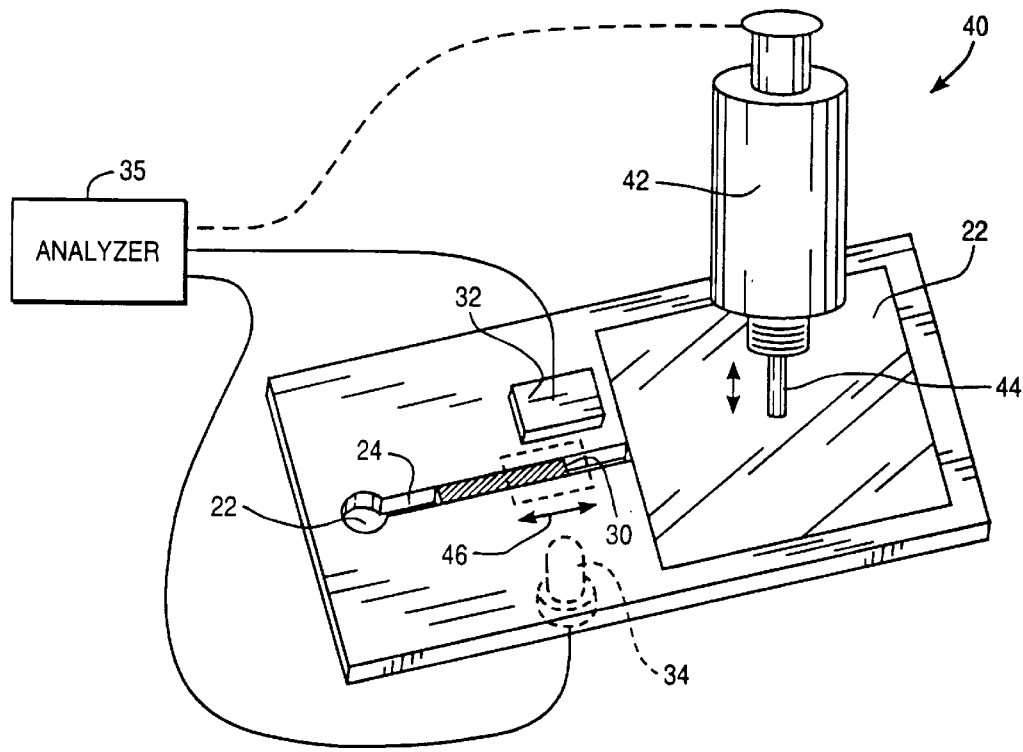
FIG_5
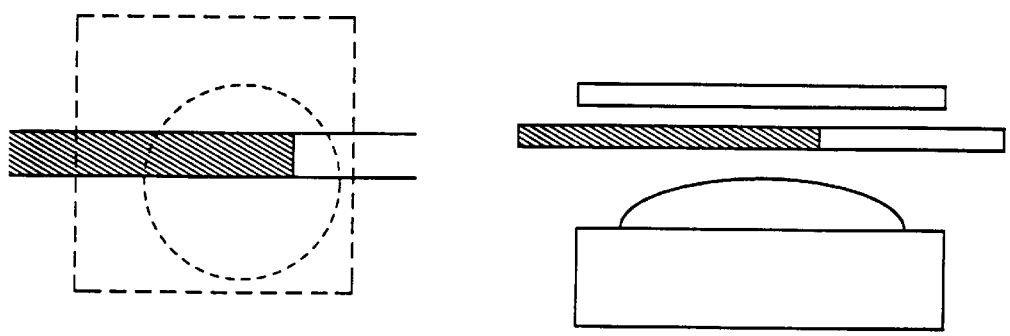
FIG_5A    FIG_5B

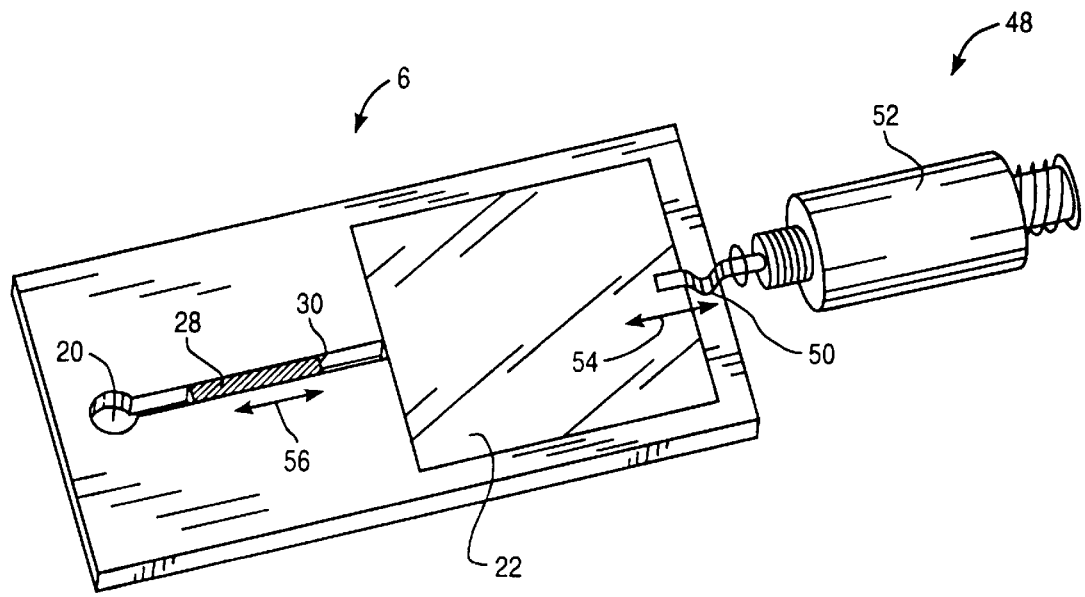
FIG_6
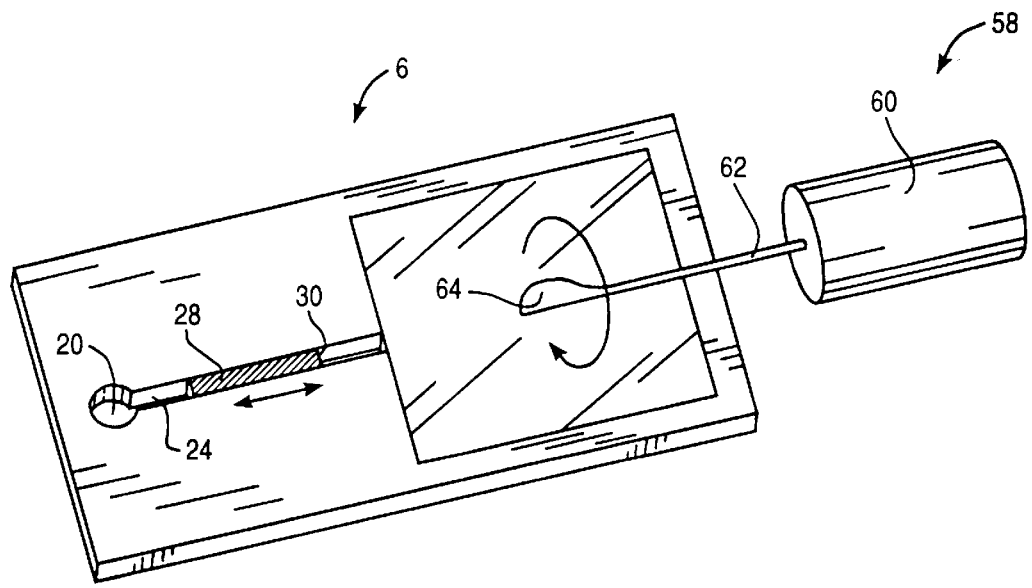
FIG_7

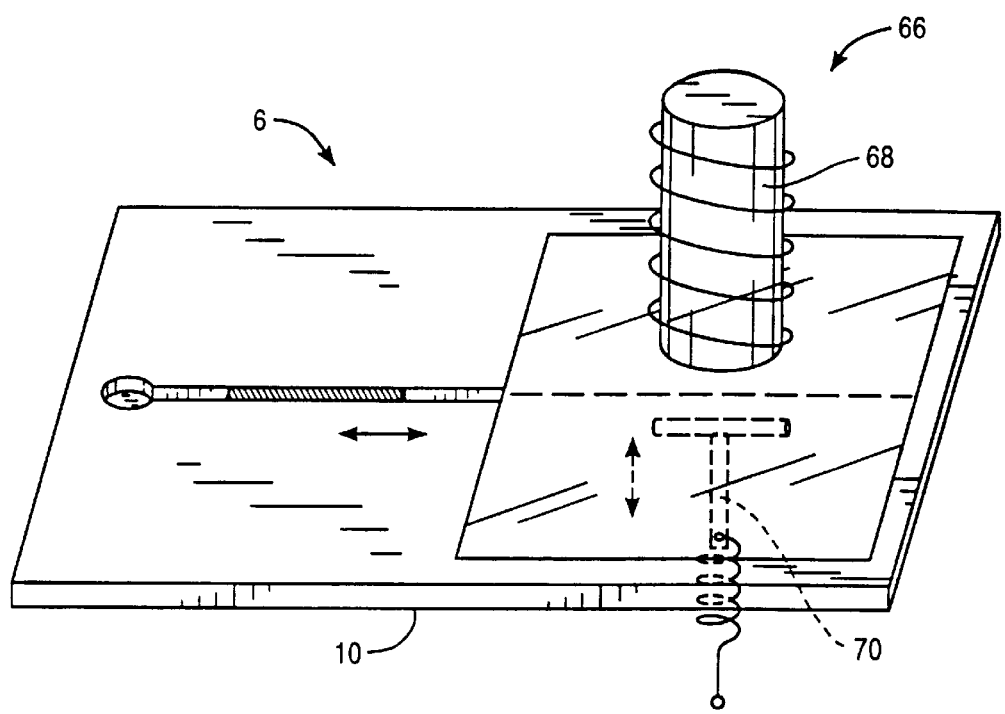
FIG_8
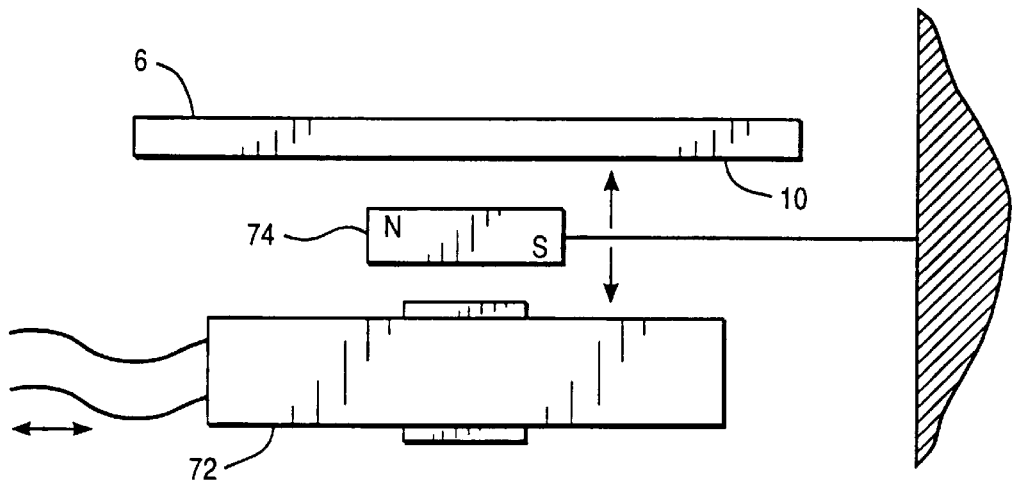
FIG_9

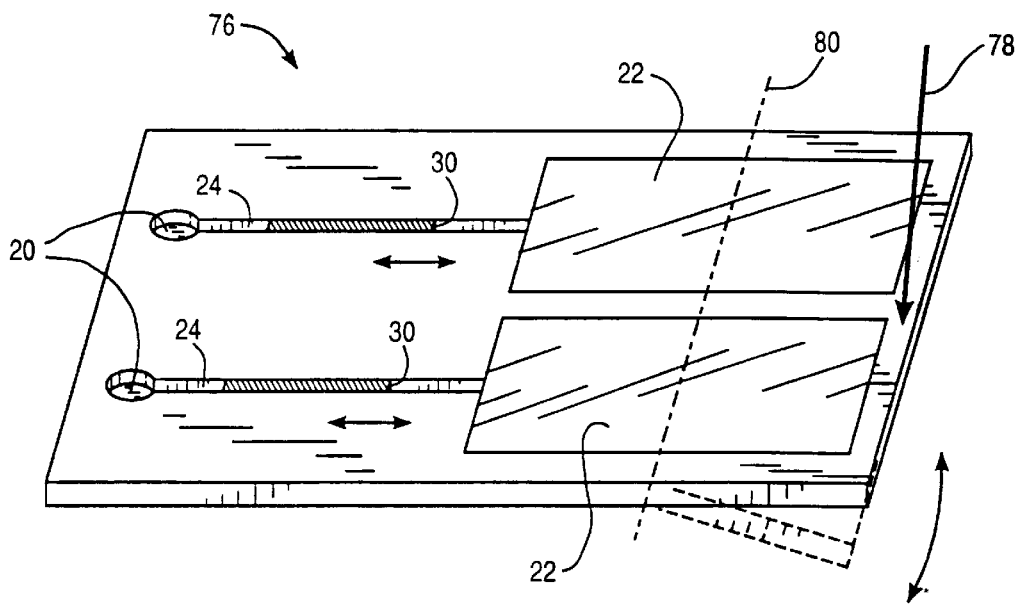
FIG_10
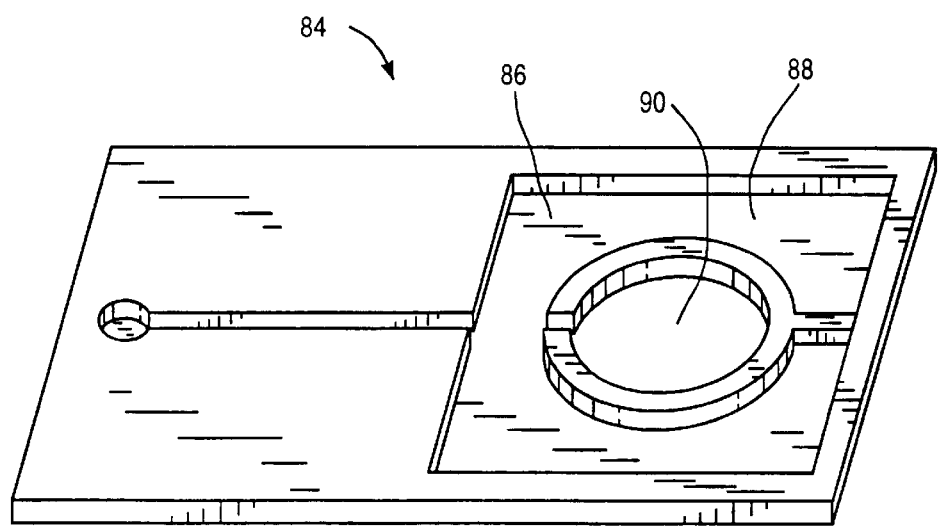
FIG_11

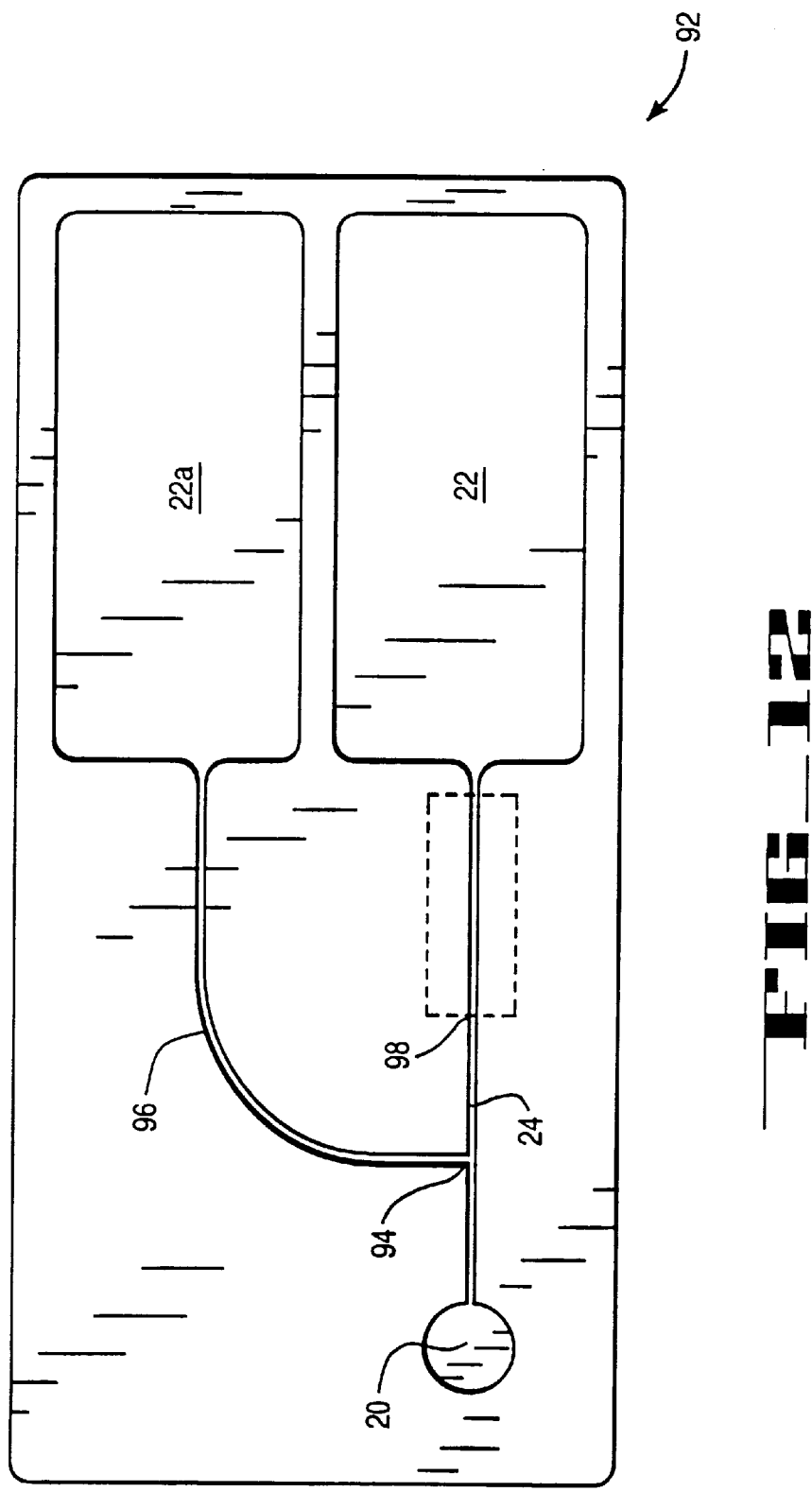

FLOW DETECTION APPARATUS AND METHOD

CROSS-REFERENCE TO RELATED APPLICATION

This application is a continuation of and claims the benefit of U.S. application Ser. No. 08/579,367, filed Dec. 27, 1995, now U.S. Pat. No. 5,736,404, the disclosure of which is incorporated by reference.

This is related to U.S. patent application Ser. No. 08/269,253 filed Jun. 30, 1994 and entitled Sample Collection and Manipulation Apparatus and Method, now U.S. Pat No. 5,700,695, the disclosure of which is incorporated by reference.

BACKGROUND OF THE INVENTION

Flow-related characteristics of a fluid, such as changes in viscosity with temperature of a liquid, are often measured to provide important information about the fluid. The speed at which blood coagulates when subjected to a coagulation reagent has particular utility in the medical field. Numerous methods have been proposed and used to measure coagulation. Some of the methods are suitable for use using disposable cuvettes or strips. For example, U.S. Pat. No. 4,797,369 to Mintz teaches a mechanical method to detect clot formation by looking for fibrin threads as a probe is pulled from a sample/reagent mixture. Other methods use magnetic stir bars or particles that are located in the sample/reagent mixture, under the influence of an oscillating magnetic field, looking for a reduction in movement as the clot forms and gels the sample. See, for example, U.S. Pat. No. 4,849,340 to Oberhardt. Another method, shown in U.S. Pat. No. 4,756,884 to Hillman, disclose monitoring the capillary flow of a whole blood sample by observing a non-stationary speckle pattern when coherent light is scattered from the cells in the moving sample; coagulation is detected when the speckle pattern becomes stationary, indicating the cessation of sample flow in the capillary.

Air pressure has been used to move samples in a cuvette for the purpose of measuring coagulation time. For example, U.S. Pat. No. 4,725,554 to Schildknecht uses air pressure to move the sample back and forth across an edge to create a clot, and then detects the formation of the clot at the edge by measuring a change in optical absorption. Other examples are shown in U.S. Pat. Nos. 3,890,098 to Moreno and 3,486,859 to Greiner where two cups or chambers are interconnected through a capillary, and air pressure is used to transfer the liquid reagent and sample combination back and forth until a clot blocks the capillary and the increase in air back pressure is detected.

U.S. Pat. No. 5,302,348 to Cusack discloses a coagulation measurement apparatus which uses disposable cuvette, one end of which is inserted into the measurement apparatus. The cuvette includes a cup-shaped sample reservoir and a pair of open-ended passageways. Each passageway opens to the ambient environment through the sample reservoir at their proximal ends and to the ambient environment at their spaced-apart distal ends. A sample drop of blood is placed in the fluid reservoir positioned external of the apparatus. The open distal end of one of the passageways is connected to a first pump which draws a fluid sample into the first passageway. A second pump is connected to the open distal end of the second passageway and draws an unused portion of the sample into the second passageway so that no sample is left in the sample receptacle. The test sample in the first passageway is caused to oscillate back and forth through a restricted area which is preferably treated to be a more efficient clotting surface. A pair of light sensors, one on each side of the restricted area, are used to determine when the leading or trailing edge of the test sample passes a sensor. Endpoint, that is when sufficient clotting has occurred, is determined when the time for the sample to traverse the restricted region is a predetermined percentage longer than an immediately proceeding time. The rate of oscillation can be adjusted throughout a run to avoid breaking apart a weak clot with a long clotting time. A heater is located under the cuvette when inserted into the measurement apparatus to set the operating temperature for the particular chemical reaction.

SUMMARY OF THE INVENTION

The present invention is directed to a fluid detection apparatus and method by which a fluid sample tester can be made to be simpler in construction than prior art systems and can provide continuous information about the flow characteristic being measured using a disposable cartridge. The cartridge is simpler in construction and more safely disposed of than conventional cartridges.

The cartridge defines a pressure chamber, an entrance port and a passageway fluidly coupling the two. An analyte reagent is preferably positioned along the fluid passageway so that when a fluid sample is drawn through the entrance port into the passageway, the analyte reagent mixes with the fluid sample. The ends of the fluid sample define boundary surfaces positioned along the fluid passageway. Pressure is applied to the fluid sample to move at least one of the boundary surfaces along the passageway. The position of the boundary surface is continuously monitored so that continuous boundary position data is obtained. The boundary position data is analyzed to obtain a flow-related characteristic of the fluid sample. For example, speed of coagulation of a blood sample can be measured in this way. Preferably, positive and negative pressures are applied to the fluid sample so that the boundary surface oscillates along the passageway as the boundary position data is obtained.

The sample can be drawn into the passageway by temporarily reducing the volume of the pressure chamber, applying the test sample to the entrance port and then returning the volume of the pressure chamber to its original volume. Another method to draw in the sample would be to draw out a portion of the gas in the pressure chamber using, for example, a syringe having a needle cannula passing through an elastomeric septum in the wall of the pressure chamber.

The fluid sample, typically a liquid, can also be drawn into the cartridge by first heating the pressure chamber with the entrance port open to the ambient environment to reduce the density of the gas within the pressure chamber. The fluid sample is then applied to the entrance port. As the gas in the pressure chamber cools, the liquid sample is drawn into the passageway due the partial vacuum created in the pressure chamber.

One of the primary advantages of the invention is its simplicity. No fluid pumps, as are used with, for example, the Cusack apparatus, are needed. Preferably, the test sample is drawn into the cartridge by mechanically reducing the volume of the pressure chamber. Alternatively, the sample can be drawn into the cartridge by cooling the gas in the pressure chamber. Assuming cooling is brought about after first heating above ambient temperature, this provides an additional advantage upon disposal of the cuvette. That is, once a cartridge returns to ambient temperature (and once the sample is drawn into the pressure chamber by mechanically reducing the volume of the pressure chamber), the sample is effectively locked within the passageway in the cartridge since there is preferably only one opening from the ambient environment to the passageway. Thus, unlike the cuvette shown in Cusack which has openings on each end of each of its passageways, the liquid sample within the cartridge is effectively prevented from leaking out upon disposal.

A further advantage of the invention is that the amount of fluid movement necessary can be made very small if needed. For example, some coagulation assays produce a relatively fragile clot that can be easily disrupted by excessive fluid movements. With the present invention, endpoint detection with only a very small amount of fluid displacement will work with only a very small signal in the detector. This is achieved by continuously obtaining positional data and appropriate mathematical manipulation of data. In contrast, the system shown in Cusack requires enough movement to commutate between the physical limitations of the two detectors.

With the present invention the oscillatory movement of the sample within the fluid passageway is preferably accomplished by deflection of a wall of the pressure chamber. This can be accomplished in several different ways. For example, various types of solenoid drivers can be used to deflect and release one wall of the pressure chamber. Electromagnetic drivers or even bending of the pressure chamber can be used as well. The same structure used to oscillate the sample can also be used to initially reduce the volume of the pressure chamber to draw the sample into the passageway. Oscillating pressures can also be created by thermal means, that is, raising and lowering the temperature of the pressure chamber. This would be useful when the frequency of movement is not needed to be that quick.

Since the pressure chamber is sealed, no specialized pressure couplings are needed between the disposable cartridge and the tester. By keeping the entrance port of the cartridge external of the tester, the portion of the cartridge which enters the tester is completely sealed; this helps to reduce the possibility of bio-contamination of the tester from the sample or its aerosol components which, in the apparatus disclosed in the Cusack patent, pass into the tester.

Another advantage of the invention is that a disposable cartridge can be made using a very simple, inexpensive construction technique such as lamination or blow molding techniques. Precision, fluid-tight fittings are not necessary, in contrast with the cuvette of the Cusack patent.

Other features and advantages of the invention will appear from the preferred embodiment which has been set forth in detail in conjunction with the accompanying drawings.

BRIEF DESCRIPTION OF THE DRAWINGS

FIG. 1 is an overall view showing a fluid sample tester assembly, including a fluid sample tester and a cartridge, made according to the invention;

FIG. 2 is an exploded view showing the cartridge of FIG. 1 prior to assembly;

FIG. 3 schematically illustrates heating of the pressure chamber defined within the cartridge of FIG. 2 after the cartridge has been inserted into a tester of FIG. 1;

FIG. 4 schematically represents cooling the pressure chamber of the cartridge of FIG. 3 using a fan within the tester of FIG. 1 to draw the test sample from the entrance port into the passageway;

FIG. 5 is a simplified representation of the cartridge of FIG. 4 suggesting the positioning of a light source and a photodetector above one of the boundary surfaces of the liquid sample within the passageway and a solenoid driver causing a portion of the cartridge bounding the pressure chamber to flex back and forth, thus decreasing and increasing the volume of the pressure chamber, causing the boundary surface of the liquid sample to oscillate between the photodetector and light source;

FIGS. 5A and 5B are enlarged, simplified top and side views illustrating the relative positions of the photodetector, light source and the boundary surface of the liquid sample within the passageway of FIG. 5;

FIG. 6 illustrates an alternative solenoid driver used to deflect one wall of the pressure chamber using a linear motion generally parallel to the pressure chamber;

FIG. 7 illustrates a motor driver having a rotating cam used to deflect the wall of the pressure chamber in an oscillating manner;

FIGS. 8 and 9 illustrate two different electromagnetic schemes for deflecting a wall of the pressure chamber to create the oscillation of the boundary surface of the liquid sample;

FIG. 10 illustrates a cartridge similar to the cartridge of FIG. 4 but including pairs of entrance ports, pressure chambers and connecting passageways, in which the oscillating change in volume of the pressure chambers is achieved by deflection and release of one end of the cartridge so that the cartridge flexes about an axis passing through the pressure chambers, thereby increasing and decreasing the volumes of the pressure chambers to create the desired oscillatory movement of the boundary surfaces of the liquid samples;

FIG. 11 illustrates a further embodiment of the cartridge of FIG. 1 in which the pressure chamber has been divided into larger and smaller, interconnected pressure chambers in which both the pressure chambers are used to draw the liquid sample into the passageway and the smaller pressure chamber is used to create the oscillatory motion for the boundary surface of the liquid sample within the passageway when very small oscillations are desired; and FIG. 12 illustrates a further embodiment of the cartridge of FIG. 1 in which a waste channel is formed off of the passageway coupled to a secondary pressure chamber used to draw off excess fluid sample from the passageway and entrance port.

DESCRIPTION OF THE PREFERRED EMBODIMENT

FIG. 1 illustrates a fluid sample tester assembly 2 made according to the invention. Assembly 2 includes a fluid sample tester 4 and a cartridge 6. Cartridge 6 is typically disposable after use. Cartridge 6 can be made by any number of methods. One such method is suggested in FIG. 2 in which cartridge 6 comprises a top 8, a bottom 10 and a base 12 sandwiched between the top and bottom. Base 12 has an enlarged open region defining a pressure chamber interior 14, a relatively narrow passageway groove 16 terminating at pressure chamber interior 14 at one end and an enlarged end 18 at the other. Enlarged end 18 of passageway groove 16 is aligned with an entrance port 20 formed in top 8. Top 8, bottom 10 and base 12 can be made of any number of materials, such as polycarbonate, ABS or polystyrene, and are preferably secured to one another to create cartridge 6 through the use of adhesives, ultrasonic welding techniques, thermal bonding, etc. Instead of having entrance 20 preformed into top 8, entrance port 20 could be formed after assembly of top 8, bottom 10 and base 12. Once assembled, top 8, bottom 10 and base 12 define a pressure chamber 22 connected to entrance port 20 by a passageway 24.

In an embodiment designed to test coagulation of whole blood, base 12 is 0.25 mm (0.010 in.) thick, pressure chamber 22 has a volume of about 0.05 ml (0.003 in$^3$) and passageway 24 has a cross-sectional area of about 0.25 mm$^2$ (0.0004 in$^2$) and a length of about 25 mm (1 in). Entrance port 20 has a volume of about 0.020 ml (0.0012 in$^3$) from the opening 20 formed in top 8 and enlarged end 18 formed in base 12.

After placement of cartridge 6 through an entrance opening 25 in fluid sample tester 4, pressure chamber 22 can be heated in preparation for applying a fluid sample to entrance port 20. This is done to reduce the density of gas within pressure chamber 22 so that pressure chamber 22 acts as a thermal pressure chamber. To aid heating the gas, typically air, within pressure chamber 22 the surface of bottom 10 or top 8 bounding pressure chamber interior 14 is treated with, for example, carbon to create a radiation absorption surface. When placed within fluid sample tester 4, pressure chamber 22 is automatically aligned with a radiation source 26 within tester 4. Radiation source 26 is then energized for a period of time sufficient to properly heat the interior of pressure chamber 22. Other methods for heating the interior of pressure chamber 22, such as through the use of direct contact heaters or flowing heated air across cartridge 6, could be used as well. Heating could also occur external of tester 4.

After pressure chamber 22 is properly heated, an appropriate sample is applied to entrance port 20. This can be done automatically or manually, such as through the use of an eyedropper or a pipette. In a manual mode, cartridge 6, when properly positioned within tester 4, has a portion of cartridge 6 external of fluid sample tester 4 to permit user access to entrance port 20. To draw the fluid sample 28 into passageway 24, the gas within pressure chamber 22 is cooled. This can be accomplished simply by permitting the thermal mass of cartridge 6 to cool the gas within pressure chamber 22 or, as suggested by FIG. 4, a fan 30 can be used to blow cool air across cartridge 6 to help cool pressure chamber 22. Other ways of cooling pressure chamber 22, such as by the use of direct-contact Peltier heaters/coolers, can be used as well.

FIGS. 5–5B illustrate, in simplified form, the monitoring and manipulation of fluid sample 28 by fluid sample tester 4. Fluid sample 28 has a boundary surface 30 at either end. Sample 28 is positioned within passageway 24 so that the boundary surface 30 closest to pressure chamber 22 lies positioned between a photodetector 32, preferably a photodiode, and a light source 34, commonly an LED. Photodetector 32 and light source 34 are connected to an analyzer 35 used to measure, in the preferred embodiment, coagulation times for blood samples as the flow-related characteristic. To this end a coagulation reagent 36, see FIG. 2, such as thromboplastin, is applied to bottom 10 of cartridge 6 at a position aligned with passageway groove 16 so that fluid sample 28 will come in contact with and mix with reagent 36 upon being drawn into passageway 24.

In the preferred embodiment, at least top 8 and bottom 10 are transparent or translucent so that the amount of light detected by photodetector 32 depends upon the position of boundary surface 30. The initial position of boundary surface 30 is dependent on the change in temperature in, and thus the density of, the gas within pressure chamber 22. Once the temperature within pressure chamber 22 has stabilized for the period of the test, it is desired to cause boundary surface 32 to oscillate within the region of detection between photodetector 32 and light source 34. Since photodetector 32 continuously monitors the position of boundary surface 30, this permits analyzer 35 to obtain continuous boundary position data regarding the boundary surface 30.

To create this oscillatory movement of boundary surface 30, the pressure within pressure chamber 22 is changed. This can be done thermally by heating and cooling the gas within pressure chamber 22. However, heating and cooling cycle times are limited to about 1 Hz. In the preferred embodiment of FIG. 5 a solenoid driver 40 is used to mechanically flex or deflect that portion of top 8 overlying pressure chamber interior 14. Solenoid driver 40 includes a solenoid 42 which causes a solenoid shaft 44 to reciprocate. Solenoid shaft 44 presses against top 8 causing top 8 to deflect inwardly, thus reducing the volume of pressure chamber 22. On the reverse movement of solenoid shaft 44 away from pressure chamber 22, the resilience of top 8 causes top 8 to deflect back to its original position, thus enlarging pressure chamber 22 back to its original volume to cause boundary surface 30 to move back to its original position. In one embodiment, this movement in the direction of arrow 46 is about 0.25 mm (0.010 in) at a frequency of about 50 Hz. In this embodiment, passageway 24 is about 25 mm long having a cross-sectional area of about 25 mm$^2$. The total volume of sample 28 is about 5 mm$^3$ (0.0003 in$^3$) and thus occupies about 80% of passageway 24. The cycle speed of solenoid driver 40 and the amount of travel of solenoid shaft 44, which determines the distance boundary surface 30 moves in the direction of arrow 46, can change depending upon the particular test conducted and the properties of the sample being tested. For example, some coagulation assays produce a more fragile clot that can be easily disrupted by excessive fluid movement. The invention permits detection of boundary surface 30 quite accurately with only a very small amount of fluid displacement. This is not possible with conventional systems in which the boundary surface must pass to discretely positioned points for any input data to be obtained. This aspect of the present invention permits the present invention to be easily adjusted to accommodate the particular coagulation assay.

FIG. 6 illustrates an alternative embodiment of the invention in which a solenoid driver 48 has a bent shaft 50 driven by a solenoid 52. The linear movement of bent shaft 50 in the direction arrow 54 causes deflection of top 8 of cartridge 6 causing boundary surface 30 to oscillate back and forth along the direction of arrow 56.

FIG. 7 illustrates a motor driver 58, including a motor 60 and a rotating shaft 62. Shaft 62 has a cam lobe 64 at its end so that rotation of shaft 62 causes cam lobe 64 to alternatingly depress and release top 8 of cartridge 6 to create the desired oscillatory movement of boundary surface 30 of sample 28. Driver 58 provides a frequency range of about 0.1 to as high as the motor RPM if required.

FIGS. 8 and 9 disclose electromagnetic means for deflecting top 8 or bottom 10 of cartridge 6. Electromagnetic driver 66 of FIG. 8 includes an electromagnet 68 on one side of pressure chamber 22 and a spring-loaded metal shoe 70 on the other side. Alternating current flowing through electromagnet 68 alternatingly pulls and releases metal shoe 70 towards and away from it causing the metal shoe to alternatingly deflect and release bottom 10 of cartridge 6. In FIG. 9 an electromagnet 72 is used to deflect a magnet 74 towards and away from bottom 10 of cartridge 6 to create the desired oscillatory movement for boundary surface 30.

FIG. 10 illustrates a further embodiment of the invention in which a cartridge 76 has pairs of pressure chambers 22, passageways 24 and entrance ports 20. This could be used when, for example, it is desired to run two different samples at the same time or run a test sample and a standard sample for comparison. The embodiment of FIG. 10 is also different in that the oscillatory movement of boundary surfaces 30 are achieved by applying a bending force to cartridge 76 as indicated by arrow 78 for flexing the cartridge about a bend axis 80. This bending motion, illustrated in an exaggerated form by the end of cartridge 76 in dashed lines, causes a change in the volumes of pressure chambers 22.

In some cases, it may be desired to draw in the sample using pressure chamber 22 as a thermal pressure chamber but the amount of movement of boundary surface 30 is desired to be kept small because of, for example, fragile coagulation bonds. FIG. 11 illustrates a cartridge 84 defining a pressure chamber 86 including a main region 88 and auxiliary region 90. Auxiliary region 90 is smaller so that when, for example, solenoid shaft 42 of FIG. 5 is used to deflect that portion of the top of cartridge 84 it deflects only that portion overlying subsidiary region 90. This creates a much smaller change in volume for the pressure chamber 86 as opposed to pressure chamber 22 of cartridge 6. By positioning subsidiary region 90 at the position of solenoid shaft 44 used with cartridge 2, no changes need be made to the position or actuation of solenoid driver 40 of fluid sample tester 4 to achieve the reduced movement of boundary surface 30.

In some situations, it may be necessary to very accurately meter the amount fluid sample within passageway 24. FIG. 12 illustrates a cartridge 92 having a single entrance port 20, a passageway 24 and a pair of pressure chambers 22, 22A. Pressure chamber 22A is coupled to passageway 24 at position 94 by a waste channel 96. In this case, the sample to be measured is drawn into passageway 24 until the sample reaches position 98. The remainder of the sample is then drawn into waste channel 96 to leave a known quantity of sample 24 between positions 94, 98 and completely evacuating any of the sample from entrance port 20 and along passageway 24 between the entrance port and position 94. Fluid sample 28 is then moved into the region of passageway 24 so that boundary surface 30 is positioned between photodetector 32 and light source 34. While the embodiment of FIG. 12 may be useful in some situations, it is not believed that such a precise metering of the fluid sample within passageway 24 will typically be necessary.

In use, cartridge 6 is inserted into fluid sample tester 4 through entrance opening 25. Pressure chamber 22 is then heated for a desired time period. When the maximum temperature within pressure chamber 22 has been reached, or slightly thereafter, fluid sample 28 is applied to entrance port 20. Fluid sample 28 is typically a sample of about 5–10 μl of whole blood. Fluid sample tester 4 is then activated to cool the pressure chamber 20 to draw the entire fluid sample 28 into passageway 24. This causes sample 28 to come in contact with reagent 36 and provides adequate mixing between the two. Contact of the sample with the coagulation reagent initiates the start-time for the testing. Boundary surface 30 of fluid sample 28 is, if necessary, moved to place it between photodetector 32 and light source 34. The solenoid driver 40 is then actuated to cause solenoid 44 to reciprocate raising and lowering the pressure within pressure chamber 22, thus, causing boundary surface 30 to oscillate in the direction of arrow 46 while it lies between photodetector 32 and light source 34.

Analyzer 35 continuously monitors the location of boundary surface 30 by continuously obtaining boundary condition information from photodetector 32 as well as information regarding change in pressure within pressure chamber 22 due to the actuation of solenoid driver 40. This permits the analyzer 35 to not only measure the magnitude of the signal from photodetector 32, which correlates with the position of boundary surface 30, but also the phase of that signal relative to the driving pressure within pressure chamber 22 created by solenoid driver 40. The initial information obtained is used as baseline information prior to coagulation, that is before the coagulating reagent has had a chance to begin causing the whole blood sample to coagulate. The magnitude and phase of the detected optical signal from photodetector 32 is monitored until a significant change is observed. A significant change in the boundary indicates that the whole blood sample has coagulated so that an end point time is obtained.

Coagulation time can be determined by visually monitoring the output 100 from fluid sample tester 4. The output could, as shown in FIG. 1, be printed on a paper strip 102 or viewed on a screen 104. The data can also be stored on some type of magnetic media through a connection to a computer, not shown. Also, tester 4 could be made so that only raw information from photodetector 32, light source 34 and solenoid driver 40 is created and that raw data is then fed to a specially programmed computer which would perform the desired calculations and display and save the test data in any desired format.

Various algorithms can be used to efficiently and automatically determine the coagulation end point and resulting clotting time.

The above mechanical structure for oscillating the sample is preferably used to initially draw the sample into passageway 24 instead of using the thermal process discussed above. By initially exhausting a larger volume of air from chamber 22 than occurs during the oscillating movement of solenoid shaft 44, an appropriate volume of sample 28 can be drawn into passageway 24. Using mechanical means instead of thermal means to draw the sample into the passageway can result in a simpler apparatus and a simpler method of use than when the sample is initially drawn in using thermal means and oscillated using mechanical means.

Other modifications and variations can be made to disclose embodiments without departing from the subject of the invention as defined in the following claims. For example, one or more of the boundaries of pressure chamber 22 could be made of an elastomeric material rather than a flexible, resilient plastic material as in the preferred embodiments. This could be especially useful when it is desired to draw sample 28 into passageway 24 using mechanical means rather than treating pressure chamber 22 as a thermal pressure chamber. Instead of using an optical sensor, such as photodetector 32, other types of sensors, such as a capacitance sensor, a conductance sensor, or an acoustic sensor, could be used.

What is claimed is:

1. A system comprising:

a cartridge comprising a base having a fluid passageway, a pressure chamber connected to one end of the fluid passageway, and a sample port at another end of the passageway; and a fluid sample tester comprising:

means for inducing pressure changes in the pressure chamber of the cartridge, wherein sample applied through the sample port will enter the passageway and will be translated within the passageway by pressure changes in the pressure chamber; and means for continuously monitoring the boundary layer positioning within the passageway wherein the position of a boundary of the sample within the passageway may be continuously monitored over time.

2. The system according to claim 1 wherein the pressure change inducing means comprises means for cooling said pressure chamber.

3. The system according to claim 1 wherein the pressure change inducing means comprises means for cooling said pressure chamber.

4. The system according to claim 1 wherein the pressure change inducing means comprises means for heating and then cooling said pressure chamber.

5. The system according to claim 1 wherein the pressure change inducing means includes means for applying positive and negative pressure to the fluid sample so the boundary surface oscillates along the passageway.

6. The system according to claim 5 wherein the positive and negative pressure applying means comprises means for changing the volume of the pressure chamber.

7. The system according to claim 5 wherein the pressure chamber is defined in part by a resilient, flexible wall and the positive and negative pressure applying means comprises means for deflecting and releasing said wall.

8. The system according to claim 1 wherein a portion of the cartridge defining the passageway is capable of passing light therethrough and the continuous monitoring means includes a photodetector.

9. The system according to claim 8 wherein the photodetector is positioned transverse to the passageway where the cartridge is in the fluid sample tester.

10. The system according to claim 1 further comprising an analyzer is adapted to obtain coagulation characteristic of a blood fluid sample.

* * * * *